(12) United States Patent
Thoma et al.

(10) Patent No.: US 7,119,245 B1
(45) Date of Patent: Oct. 10, 2006

(54) SYNTHESIS OF AN UN-SUPPORTED, HIGH-FLOW ZSM-22 ZEOLITE MEMBRANE

(75) Inventors: Steven G. Thoma, Albuquerque, NM (US); Tina M. Nenoff, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 651 days.

(21) Appl. No.: 10/280,252

(22) Filed: Oct. 25, 2002

Related U.S. Application Data

(60) Provisional application No. 60/335,672, filed on Oct. 25, 2001.

(51) Int. Cl.
  *B01J 21/00* (2006.01)
  *B01J 29/00* (2006.01)
  *C07C 7/00* (2006.01)

(52) U.S. Cl. .......................... 585/820; 502/77; 208/46; 208/106; 208/111.15; 208/113; 208/118; 423/703

(58) Field of Classification Search ................ 208/46, 208/106, 111.15, 113, 118; 423/328, 703; 502/77; 585/475, 820
See application file for complete search history.

(56) References Cited

U.S. PATENT DOCUMENTS

| | | | | |
|---|---|---|---|---|
| 4,556,477 A | * | 12/1985 | Dwyer | 208/111.15 |
| 4,902,406 A | * | 2/1990 | Valyocsik | 208/118 |
| 5,063,038 A | * | 11/1991 | Kirker et al. | 423/703 |
| 5,336,478 A | | 8/1994 | Dwyer et al. | 423/78 |
| 5,866,096 A | | 2/1999 | Verduijn et al. | 423/702 |
| 6,207,871 B1 | * | 3/2001 | Hellring et al. | 585/475 |

OTHER PUBLICATIONS

Thoma, S. G., Trudell, D. E., Bonhomme, F., and Nenoff, T. M., Vapor phase transport synthesis of un-supported ZSM-22 catalytic membranes, Microporous and Mesoporous Materials, vol. 50, Issue 1, Dec. 15, 2001, pp. 33-39. Available online Oct. 14, 2001.*

Thoma, Trudell, Bonhomme and Nenoff, "*Vapor Phase Transport Synthesis of Un-Supported ZSM-22 Catalytic Membranes*", Dec. 15, 2001, pp. 33-39.

Thoma and Nenoff, "*Vapor Phase Transport Synthesis of Zeolites from Sol Gel Precursors*", Dec. 2000, pp. 295-305.

Matsukata, Nishiyama and Ueyama, "*Preparation of a Thin Zeolitic Membrane*", vol. 84 1994, pp. 1183-1190.

(Continued)

*Primary Examiner*—Glenn Caldarola
*Assistant Examiner*—Prem C. Singh
(74) *Attorney, Agent, or Firm*—Robert D. Watson

(57) ABSTRACT

Novel methods for synthesizing wholly un-supported, high-flow catalytic membranes consisting of 100% crystalline ZSM-22 crystals with no binder phase, having sufficient porosity to allow high Weight Hourly Space Velocities of feedstock to pass through without generating back pressure. The ZSM-22 membranes perform favorably to existing bulk ZSM-22 catalysts (e.g., via 1-butene conversion and selectivity). The method of membrane synthesis, based on Vapor Phase Transport, allows free-standing, binder-less membranes to be fabricated in varied geometries and sizes so that membranes can be tailor-made for particular geometries applications. The ZSM-22 precursor gel may be consolidated into a semi-cohesive body prior to vapor phase crystallization, for example, by uniaxial pressing. These crystalline membranes may be modified by ion exchange, pore ion exchange, framework exchange, synthesis modification techniques to incorporate other elements into the framework, such as K, H, Mg, Zn, V, Ga, and Pt.

52 Claims, 4 Drawing Sheets

OTHER PUBLICATIONS

Dong, Dou, Zhao and Gao, "Synthesis of Membranes of Zeolites ZSM-5 and ZSM-35 by the Vapour Phase Method", 1992, pp. 1056-1058.

Nishiyama, Ueyama and Matsukata, "Gas Permeation through Zeolite-Alumina Composite Membranes", vol. 43, No. 11A 1997, pp. 2724-2730.

Kiricsi, Shimizu, Kiyozumi, Toba, Niwa & Mizukami, "Catalytic Activity of a Zeolite Disc Synthesized through Solid-State Reactions", 1998, pp. 453-459.

Nishiyama, Ueyama & Matsukata, Synthesis of Defect-Free Zeolite-Alumina Composite Membranes by a Vapor-phase Transport Method, Apr. 1996, pp. 299-308.

Kumar, N., et al., "*Synthesis and characterization of H-ZSM-22, Zn-H-ZSM-22 and Ga-H-ZAM-22 zeolite catalysts and their catalytic activity in the aromatization of n-butane*", Applied Catalysis A: General, 139 (1996) 189-199.

Sano, Tsueneji, et al., "Growth Process of ZSM-5 Zeolite Film", Bull. Chem. Soc. Jpn., 65, (1992) 146-154.

Tsikoyiannis, J.G., and Haag, W.O., "*Synthesis and characterization of a pure zeolite membrane*", ZEOLITES, Feb. 12, 1992, 126-130.

Baeck, S.H., and Lee, W.Y., "Dealuminmation of Mg-ZSM-22 and its use in the skeletal isomerization of 1-butene to isobutene", Applied Catalysis A: General, 168 (1998) 171-177.

\* cited by examiner

SYNTHESIS OF AN UN-SUPPORTED, HIGH-FLOW ZSM-22 ZEOLITE MEMBRANE

CROSS-REFERENCE TO RELATED APPLICATIONS

This application claims the benefit of U.S. provisional application Ser. No. 60/335,672 filed Oct. 25, 2001, "Novel Synthesis of an Un-Supported, High-Flow ZSM-22 Zeolite Membrane for On-Line Catalytic Treatment of Hydrocarbon Streams", by S. G. Thoma and T. M. Nenoff, which is incorporated herein by reference.

FEDERALLY SPONSORED RESEARCH

The United States Government has rights in this invention pursuant to Department of Energy Contract No. DE-AC04-94AL85000 with Sandia Corporation.

BACKGROUND OF THE INVENTION

This invention relates generally to catalytic materials and membranes that are used in the chemical and petroleum refining industry, and more specifically to high-flow catalytic zeolite membranes and methods of synthesis.

Zeolites comprise microporous inorganic aluminosilicates with pore diameters in the 3–7 Å range. They are commonly used in bulk form for gas separations, as catalysts, and for dehydration.

The commercial market for industrial membranes is growing rapidly and is expected to reach $3.5 billion by 2005. Zeolitic membranes figure prominently in this rapidly developing area. Development of new methods of zeolite synthesis and new methods of membrane synthesis will greatly expand the variety of organic and inorganic molecular separations possible. Substitution of zeolites in membrane form, as opposed to a loose powder, would allow these industrial processes to operate using continuous flow reactors, as well as eliminate the use of binders, thereby substantially reducing energy consumption and overall operating costs.

A particularly useful zeolite, ZSM-22, is currently used as a catalyst in many industrially important applications, including: (a) olefin isomerization (specifically production of MTBE, among others); (b) catalytic dewaxing (refining of heavy oils); (c) toluene alkylation (for production of p-xylene); (d) isomerization of aromatic compounds (for production of p-xylene); and (e) production of jet fuels. All of these industrial processes currently utilize the zeolite in bulk form (e.g., powders, granules and pellets held together with binder phases) in batch type reactors because ZSM-22 is not commercially available in membrane form.

Historically, zeolites with the high-flow, open TON crystal structure were synthesized first as Theta-1 [1], KZ-2 [2], Nu-10 [3], and ZSM-22 [4] via hydrothermal methods. These were later determined to have identical crystal structures though varied morphology [5]. This family of zeolites is characterized by high aspect ratio crystals with uni-dimensional pores formed by 10-member rings. The shape selective and catalytic properties of TON zeolites are widely known, though there is some disagreement as to the source of these properties [6–10]. Platinum doping [11], ion exchange [12], framework metal substitution [13], and silicon deposition [14] are all methods shown to be useful in enhancing desirable properties for industrial applications. In particular, ZSM-22 has the ability to isomerize 1-butene to 2-butene, which is a precursor in the manufacture of methyl tert-butyl ether [15].

Zeolites are typically synthesized by hydrothermal or solvothermal methods; ZSM-22 solely by hydrothermal methods [1–4]. Recently, however, Vapor Phase Transport (VPT) and Dry Gel Conversion (DGC) have been used to synthesize a variety of zeolites and zeolite membranes [16–22]. VPT refers to conversion of a dry, amorphous precursor into a fully crystalline material via contact with a vapor phase organic-water mixture, while DGC refers to conversion of a dry, amorphous precursor into a fully crystalline material via contact with only vapor phase water.

One difference between the vapor phase method versus traditional hydrothermal methods is that rather than dissolving or dispersing all the ingredients into a solution (i.e. into excess solvent), the ingredients, in proper proportion are mixed together and gelled into a non-crystalline, solid, precursor. A standard definition of gelation is forming a continuous, 3-dimensional interconnected (chemically bonded) network throughout the entire solution—the solution is transformed from a liquid to a solid without significant loss of volume or solvent. Such gels typically contain a lot of solvent, alcohols, water, etc. Gels are not really 'solids', but super viscous liquids—in the same manner as glass is a liquid—because they contain no long range structural order.

In order to crystallize this material, energy in the form of heat, and some additional organics are added (in the vapor phase). Some water may also be necessary to allow bond breakage, without which molecular rearrangement (i.e. crystallization) could not take place. The organics help to form nucleation sites (together with the inorganic gel) from which the crystal grows. A particular chemistry gel, i.e. elements in the correct range of proportions, as well as an adequate—but often not excessive—amount of vapor phase organic & water will grow crystals.

The type of vapor phase organic(s), the ratio of water to organic, and water/organic to solid, the type of chemical elements, the ratio of chemical elements, the degree of association between the chemical elements (largely determined/fixed at the point of gelation by the gelation method but also a factor of temperature and aging of gel), amount and type of liquid solvent used to form the pre-gel solution, the type and form of the chemicals used in the pre-gel solution—all help determine which crystal phase will nucleate and grow.

In VPT and DGC the outcome of the crystallization process can be controlled to a much greater degree because the precursor chemicals in the gel are "frozen", whereas in hydrothermal synthesis all of the ingredients are just dumped into a solution and heated—there is much less control, or no control at all, of the factors listed above.

A membrane form of ZSM-22 could have different properties, such as: (1) a robust structure due to the crystal intergrowth, allowing it to have sufficient strength to be entirely un-supported; (2) a ZSM-22 membrane made up of 100% pure crystalline zeolites without any binder phase would have no impurities or additional components that could possibly contaminate or interfere with processing of a hydrocarbon stream; (3) a ZSM-22 membrane could be high-flow, where high volumes (high Weight Hourly Space Velocities) of feed stock may be passed through the membrane past the crystals that have a very high surface area for catalysis without fouling or build-up of back-pressure, which would be an extremely important property for industrial membrane processes; and (4) ZSM-22 membranes could be fabricated and manufactured in a variety of sizes, thicknesses, shapes, and non-planar curvatures that could be tailored to meet a wide variety of specific needs. Synthesis of ZSM-22 membranes using VPT and/or DGC methods could reduce manufacturing costs since there would be no excess or wasted materials, and since there would be no need to add binders, which adds additional process steps.

A need remains, therefore, for a method of synthesizing un-supported, high-flow ZSM-22 zeolite membranes that do not have a binder phase. Against this background, the present invention was developed.

SUMMARY OF THE INVENTION

The present inventions relates to novel methods of synthesizing wholly un-supported, high-flow catalytic membranes consisting of 100% crystalline ZSM-22 crystals with no binder phase, having sufficient porosity to allow high Weight Hourly Space Velocities of feedstock to pass through without generating back pressure. The ZSM-22 membranes perform favorably to existing bulk ZSM-22 catalysts (e.g., via 1-butene conversion and selectivity). The method of membrane synthesis, based on Vapor Phase Transport, allows free-standing, binder-less membranes to be fabricated in varied geometries and sizes so that membranes can be tailor-made for particular geometries applications. The ZSM-22 precursor gel may be consolidated into a semi-cohesive body prior to vapor phase crystallization, for example, by uniaxial pressing. These crystalline membranes may be modified by ion exchange, pore ion exchange, framework exchange, synthesis modification techniques to incorporate other elements into the framework, such as K, H, Mg, Zn, V, Ga, and Pt.

BRIEF DESCRIPTION OF THE DRAWINGS

The accompanying drawings, which are incorporated in and form part of the specification, illustrate various examples of the present invention and, together with the detailed description, serve to explain the principles of the invention.

DETAILED DESCRIPTION OF THE INVENTION

Figure 1:
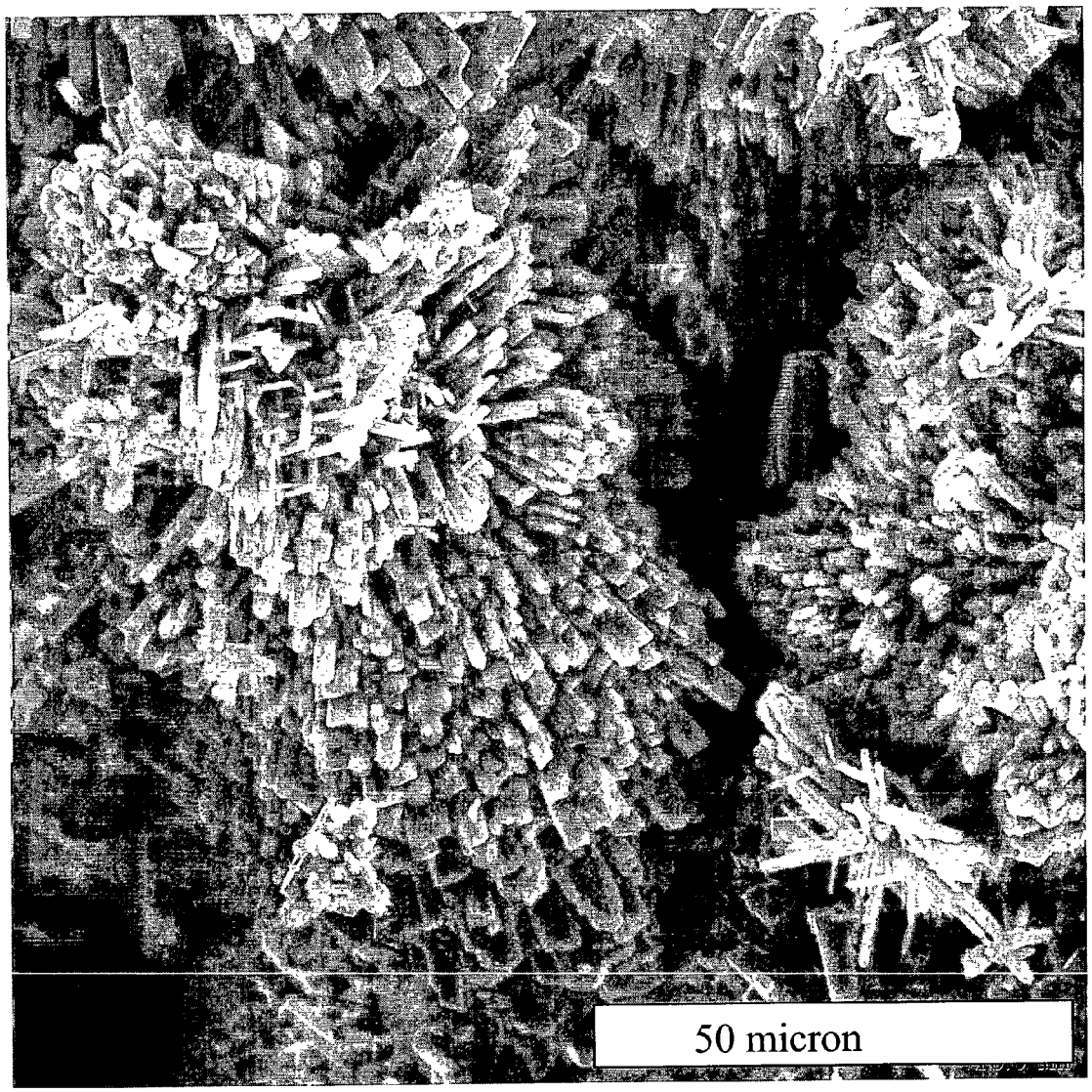
FIG. 1 shows a SEM image of bulk ZSM-22 crystals produced by an embodiment of the present invention.

Un-supported, high-flow ZSM-22 membranes that consist essentially of the crystalline zeolite may be synthesized by either VPT or DGC methods. Crystal intergrowth imparts mechanical strength to the membranes, which allows them to be formed in various sizes, thickness, shapes, and non-planar curvatures. This type of membrane can be manufactured with a high porosity ("high-flow"), which permits high volumes of feedstock to be passed through the membrane without fouling or build-up of backpressure (important properties for industrial membrane processes). Furthermore, since the entire membrane consists essentially of zeolite crystals, there are essentially no impurities or additional components that could possibly contaminate or interfere with a hydrocarbon stream (such as binder phases). Also, VPT and DGC synthesis methods produce essentially no excess or wasted material, which reduce operating costs during synthesis and minimizes the generation of hazardous wastes. A ZSM-22 membrane of this type does not need to use a binder phase to hold the crystals together; hence, the additional processing steps used in the synthesis of bulk ZSM-22 are reduced.

ZSM-22 may be synthesized as follows. A clear amorphous gel containing all the elemental constituents of ZSM-22, in the appropriate proportions, is formed. The gel is dried and powdered. The gel is then crystallized into ZSM-22 by exposing it to vapor of an organic solvent with mild heating. If the powder is thus crystallized as is (loose), bulk ZSM-22 is prepared. However, if prior to VPT or DGC crystallization the powder is pre-formed into a semi-cohesive disc or other shape (e.g., by pressing or slip-casting) and this semi-cohesive disc exposed to the organic vapor with mild heating, a fully crystalline, un-supported disc-shaped membrane is formed consisting of inter-grown, essentially pure ZSM-22 crystals without any binder phase. In this manner, any size and shape membrane may be fabricated. Furthermore, modifications in the chemical recipe and gel processing during and after synthesis allow the crystal size and shape to be altered in a controlled fashion thereby giving the user some control over membrane properties such as porosity and density. Also, chemical dopants may be included in this synthesis process, as may be needed by specific industrial processes.

A first embodiment of a process for synthesizing ZSM-22 zeolite crystals according to the present invention may comprise: a) preparing a precursor gel containing all of the elemental constituents of ZSM-22 by mixing a solution containing a source of aluminum, an alcohol, a source of silica, a base and water, whereby a precursor gel forms; b) then drying the precursor gel; c) then grinding the dried precursor gel into a powder; and d) then exposing the powdered dried precursor gel to vapors of a solvent mixture at a temperature and exposure time sufficient to form ZSM-22 zeolite crystals. The source of aluminum may comprise aluminum tri-sec butoxide (ASB). The source of silica may comprise tetramethylorthosilicate (TMOS). The alcohol may be 2-propanol, butanol, and iso-butanol, or combinations thereof. The base may be KOH or NaOH. The powdered precursor gel may be exposed to vapors of the solvent mixture in an autoclave heated at a temperature above the boiling points of the solvents in the solvent mixture, and for an exposure time sufficient to form ZSM-22 zeolite crystals. The autoclave may be heated to approximately 130–190 C during crystallization. The precursor gel may be treated with 1,6-diaminohexane (DAH).

An un-supported membrane of ZSM-22 crystals may be produced by consolidating the powdered dried precursor gel described above into a semi-cohesive body without using any binder phase, prior to exposing the powdered dried precursor gel to vapors of a solvent mixture at a temperature and exposure time sufficient to form ZSM-22 zeolite crystals. The powdered precursor gel may be placed into a rigid die and then loaded with a uniaxial pressure of between about 5000 psi and about 10,000 psi at about room temperature.

An alternative method of producing a semi-cohesive body may comprise preparing a slurry containing the dried powdered precursor gel and then slip-casting the slurry in a mold to form a semi-cohesive body without using any binder phase, prior to exposing the powdered dried precursor gel to vapors of a solvent mixture at a temperature and exposure time sufficient to form ZSM-22 zeolite crystals. The slurry may comprise a dispersing agent selected from water, a polar solvent, an alcohol, and tetrahydrofuran (THF), and combinations thereof.

In some embodiments of the present invention, the precursor gel may have a composition with a molar ratio of approximately 1 Al:10–15 K: 40–250 Si.

In other embodiments of the present invention, the precursor gel may have a composition with a molar ratio of approximately 1 Al:12 K:182 Si.

In other embodiments, the precursor gel may have the solvent mixture comprising a mixture of water and an organic solvent selected from ethylenediamine (En), triethylamine ($Et_3N$), diethylamine ($Et_2N$), aniline, and diaminopropane (DAP), and combinations thereof.

In other embodiments of the present invention, the solvent mixture may comprise diethylamine and water in a molar ratio of 1 diethylamine:3 $H_2O$.

In other embodiments of the present invention, the autoclave temperature may be approximately 170 C and the exposure time may be approximately 11 days.

In other embodiments of the present invention, the ZSM-22 zeolite crystals may comprise a composition with a molar ratio of approximately 115 $SiO_2$:0.5$Al_2O_3$:0.8$M_2O$:5.6$Et_2N$: 18.0$H_2O$ if M=monovalent cation or 115 $SiO_2$:0.5$Al_2O_3$: 0.8MO:5.6$Et_2N$, 18.0; $H_2O$ if M=divalent cation.

In other embodiments of the present invention, the ZSM-22 zeolite crystals may be modified with an element selected from K, H, Mg, Zn, V, Ga, and Pt, and combinations thereof.

In other embodiments of the present invention, the ZSM-22 zeolite crystals may be ion exchanged under aqueous condition with alkali or alkali earth cations.

In other embodiments of the present invention, Mg may be substituted for Al during post-synthesis framework modification of the ZSM-22 zeolite crystals.

In other embodiments of the present invention, at least one of H, Zn, and Ga may be substituted for the as-synthesized K during pore element ion-exchange of ZSM-22 zeolite In other embodiments of the present invention, at least one of V and Ga may be substituted into the ASM-22 framework during synthesis of ZSM-22 zeolite crystals.

In other embodiments of the present invention, the precursor gel may have a molar ratio of approximately 1.0 Al:12.5 K:182.0 Si.

In other embodiments of the present invention, the dried precursor gel may contain less than 5 wt % of water.

In other embodiments of the present invention, the ZSM-22 zeolite crystals formed after autoclaving may be rinsed in water, methanol, and acetone, and then dried in air.

In other embodiments of the present invention, the ZSM-22 crystals may be calcined. Calcining the ZSM-22 crystals may comprise heating the ZSM-22 crystals at approximately 550 C for about 1 hour in an oxygen atmosphere.

In other embodiments of the present invention, the ratio of the mass of water to the mass of the precursor gel is greater than approximately 13.5.

Another embodiment of a process for synthesizing ZSM-22 zeolite crystals according to the present invention may comprise: a) preparing an precursor gel containing all of the elemental constituents of ZSM-22 by: (1) preparing a solution of base and water; (2) dissolving an equivalent molar amount of aluminum metal into the aqueous base solution; and (3) adding the product produced by step (2) to a mixture of a source of silica and an alcohol; whereby the precursor gel forms; b) then drying the precursor gel; c) then grinding the dried precursor gel into a powder; and d) then exposing the powdered dried precursor gel to vapors of a solvent mixture at a temperature and exposure time sufficient to form ZSM-22 zeolite crystals. The source of silica may comprise tetramethylorthosilicate (TMOS). The alcohol may be 2-propanol, butanol, and iso-butanol, or combinations thereof. The base may be KOH or NaOH. The powdered precursor gel may be exposed to vapors of the solvent mixture in an autoclave heated at a temperature above the boiling points of the solvents in the solvent mixture, and for an exposure time sufficient to form ZSM-22 zeolite crystals. The autoclave may be heated to approximately 130–190 C during crystallization. The powdered dried precursor gel may be consolidated into a semi-cohesive body without using any binder phase, by applying pressure prior to exposing the powdered dried precursor gel to vapors of a solvent mixture at a temperature and exposure time sufficient to form ZSM-22 zeolite crystals. The powdered precursor gel may be placed into a rigid die and then loaded with a uniaxial pressure of between about 5000 psi and about 10,000 psi at about room temperature.

In other embodiments of the present invention, the precursor gel may be treated with 1,6-diaminohexane (DAH).

In other embodiments of the present invention, the precursor gel may comprise an Al:Si molar ratio of 1:44 to 1:85.

In other embodiments of the present invention, the solvent mixture may comprise a mixture of diethylamine and water in a molar ratio of 1 diethylamine:3$H_2O$.

In other embodiments of the present invention, the autoclave temperature may be approximately 170 C and the exposure time may be approximately 11 days.

In other embodiments of the present invention, the precursor gel may comprise an Al:Si molar ratio of approximately 115.

In other embodiments of the present invention, the Si:Al molar ratio of the precursor gel may be between approximately 42 and approximately 248.

In other embodiments of the present invention, the powdered precursor gel may be consolidated into a semi-cohesive body without using any binder phase.

In other embodiments of the present invention, a ZSM-22 crystalline membrane may be produced by any the processes described above. The membrane may be un-supported, and may have a high-flow property. The ZSM-22 crystalline membrane may have a thickness greater than approximately 0.1 inches. The ZSM-22 crystalline membrane may have a bulk density of approximately 0.77 g/cc and may have a helium density of approximately 1.9 g/cc.

The ZSM-22 cyrstalline membrane may have a bulk density of between ⅓ and ⅔ the density of a ZSM-22 crystal.

In other embodiments of the present invention, an industrial process for treating a substance may comprise passing the substance through a ZSM-22 crystalline membrane produced by any of the processes described above.

Examples of Synthesis Methods

Precursor gels were prepared by mixing a clear solution containing 0.025 g of aluminum tri-sec butoxide (ASB), 1.0 g 2-propanol, and 2.70 g TMOS with a solution of 1.3 g of 1.0 M KOH and 5.6 g $H_2O$. Within minutes, a clear, rigid gel with no free liquid was obtained, which was dried in air at 50° C. for 24 hours and ground to a fine powder. The resultant gel has a molar ratio of 1.0 Al: 12.5 K: 182.0 Si, based on reactant ratios.

Other precursor gels were prepared by substituting aluminum metal for ASB as the aluminum source. This was done by fully dissolving an equivalent molar amount of aluminum metal into the KOH/water solution, which was then added to the TMOS/2-propanol solution. A clear rigid gel was formed, which was then processed identically to the untreated ASB gel. Also, some of the ASB gel was impregnated with 1.0 M 1–6diaminohexane (DAH) in ethanol and allowed to air dry overnight. These gels were also processed thereafter identically to the original ASB gel. Typical moisture content for all 50° C. dried gels is less than 5 weight percent as determined by thermal analysis.

For VPT crystallization of bulk ZSM-22, a small amount of dried gel was placed in a raised Teflon holder inside a Teflon lined steel autoclave. The configuration of the holder was such that only vapor from the solvent mixture would be able to contact the powdered gel. Various molar mixtures of water, ethylenediamine (En), triethylamine ($Et_3N$), diethylamine ($Et_2N$), aniline, and diaminopropane (DAP) were transferred directly to the bottom of the reaction vessel. The total solvent charge was 0.04 mole, and the mass of gel was varied between 0.02 and 0.5 gram. The charged autoclaves were placed in an oven with temperatures and times ranging from 130–190° C. and 4–12 days, respectively. Afterward, the recovered product was rinsed with water, methanol, and acetone, and air dried.

To prepare membranes, 0.2 grams of dried precursor gel was placed into a 0.5 inch diameter stainless steel die and isostatically pressed under 7500 psi at room temperature and without binder to produce a semi-cohesive disc. The semi-cohesive disc was then placed in a Teflon holder and crystallized in the same manner as the unconsolidated powder (i.e., by VPT).

After the crystallization, rinsing, and drying, samples were calcined at 550° C. under oxygen using a ramp rate of 1° C./minute from room temperature to 200° C. and a 0.1° C./min ramp rate from 200 to 550° C. After holding at 550° C. for one hour the oven was allowed to cool uncontrolled. The membranes were removed and used without further treatment for catalytic testing.

Characterization

Powder X-Ray diffraction (XRD) data were collected on a Siemens D500 diffractometer using Cu-Kα radiation. SEM images were recorded using a JEOL T300 scanning electron microscope (SEM) and Iridium (IXRF Systems) software. Thermal analysis was performed using a TA Instruments SDT 2960 simultaneous Thermo Gravimetric Analyzer—Differential Thermal Analyzer (TGA-DTA). Skeletal densities were determined using a Micromeritics AccuPyc 1330 helium pycnometer. Fourier Transform—Infrared (FTIR) spectroscopy was performed using a Perkin-Elmer Spectrum GX FTIR. Elemental analysis was performed by Galbraith Inc (Knoxville, Tenn.) using Inductively Coupled Plasma Spectroscopy for Al, Si, and K determination, and combustion methods for C, H, and N.

Catalysis: 1-butene Isomerization

An un-supported, high-flow ZSM-22 membrane disc was placed in a sample holder such that the reactant gas was directed through the membrane. The sample holder was placed in a tube furnace and the zeolite membrane activated under flowing He at 550° C. overnight. After cooling to 420° C., the helium stream was replaced by a 20 volume-% 1-butene (Aldrich 99+%)-helium mixture. Flow rates were varied between 20 SCCM and 125 SCCM, corresponding to weight hourly space velocities (WHSV) of 2.8 and 17.3, respectively. Analysis of reaction products downstream of the membrane was performed using an HP 5890 gas chromatograph equipped with an HP-Plot column maintained at 100° C.

Results and Discussion

The results of crystallization experiments using the ASB derived gel at various combinations of time, temperature, and solvent mixture are given in Table 1. From the six experiments in this set that yielded ZSM-22, experiment 15 did not contain any impurity phases, and so those conditions were chosen for further experimentation (170° C., 1 $Et_2N$:3 $H_2O$, 11 days).

Figure 2:
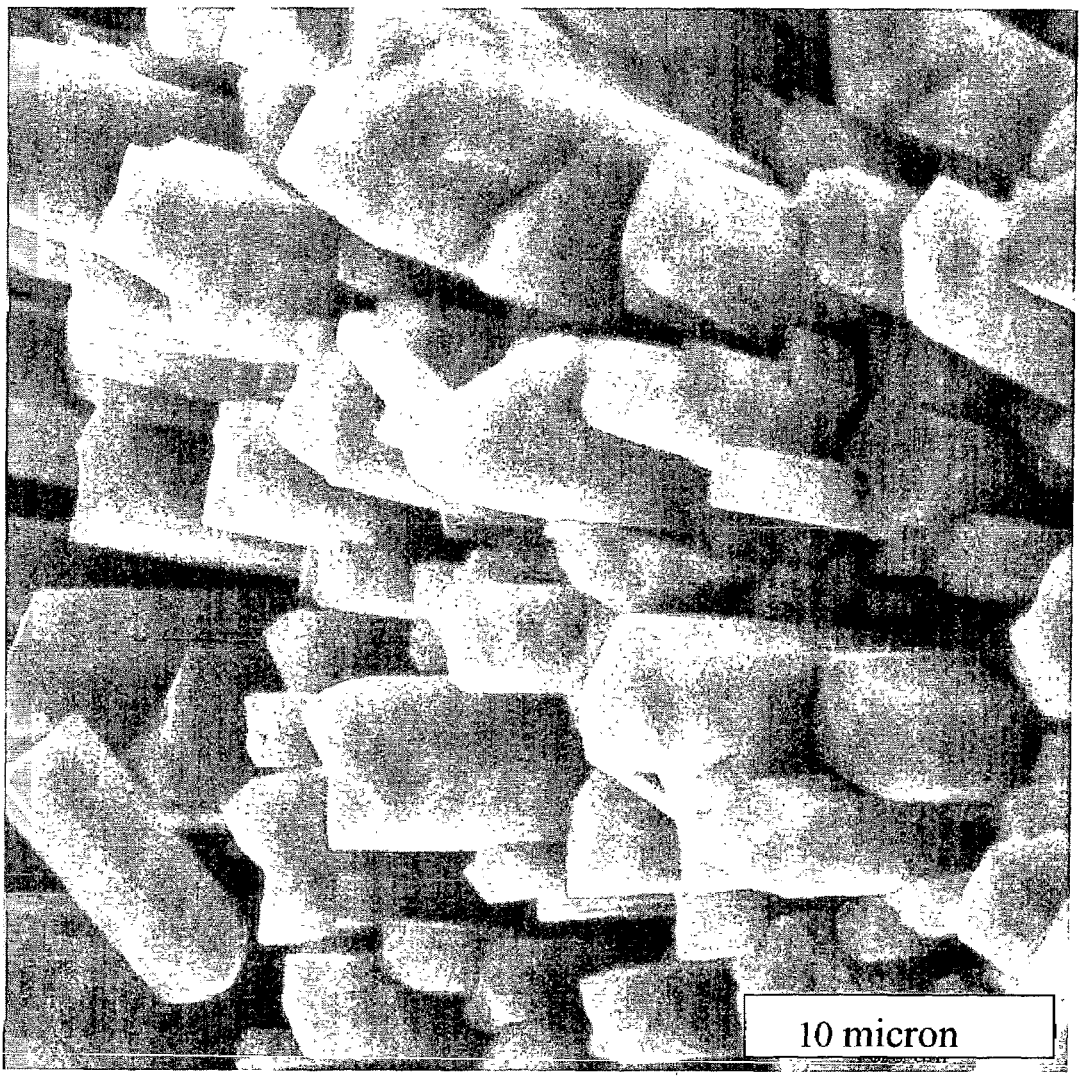
FIG. 2 shows a SEM image of bulk ZSM-22 crystals produced by an embodiment of the present invention.

The Rietveld refinement [25] of the powder diffraction pattern of this sample, based on the ZSM-22 structural model of Marler [26] (space-group C m c $2_1$) converged satisfactorily to $R_{Bragg}$=6.34% with cell parameters a=13.831(1)Å, b=17.372(2)Å and c=5.0292(5)Å. Elemental and thermal analysis showed this sample to have a composition of $115SiO_2 \cdot 0.5Al_2O_3 \cdot 0.8K_2O \cdot 5.6Et_2N \cdot 18.0H_2O$. The calculated and measured densities are 1.98 and 2.04 g/cc, respectively. SEM micrographs of these crystals are presented in FIGS. 1 and 2.

Two different procedures were developed to ensure phase purity under a broader range of synthesis conditions: 1) substitution of aluminum metal as the aluminum source in the precursor gel and 2) pre-treatment of the original ASB derived gel with DAH. Crystallizations carried out using 1 $Et_2N$:$3H_2O$ vapor for 7–12 days at 170° C. on either of these gels yielded consistently pure crystalline product (see Tables 2 and 3). Presumably, the use of aluminum metal reduced the amount of insoluble oxide species, leading to a more consistent product.

The role of the DAH, however, was unclear. Although it has been shown that both DAH [7] and $Et_2N$ [26] reside intact in ZSM-22 pores following hydrothermal synthesis, it appears in this work that the DAH decomposed during synthesis. Chemical and thermal analysis showed that all of the fully crystalline ZSM-22 samples had an $SiO_2$: $Et_2N$ ratio between 21 and 25, regardless of the gel recipe used. Yet the ZSM-22 crystallized from DAH treated gel had an additional 2–4 weight percent carbon content (than ZSM-22 derived from non-DAH treated gel), but without the corresponding increase in nitrogen, which would indicate decomposition of the amine. Furthermore, the post synthesis liquid was colorless in all experiments that did not contain DAH, but opaque brown in the DAH containing systems, also suggesting amine decomposition.

FTIR analysis aided in product analysis but was not useful in clarifying the role of the organic molecules. It showed that the Si—O—Si asymmetric stretch shifted toward lower wavelengths with increasing Al content, consistent with previously observed behavior [27]. The presence of organics in the crystalline samples was clearly indicated by various C—H modes in the 1350–1650 $cm^{-1}$ region, although in all cases the vibrations were too weak to assess whether the spectra was due to intact organic molecules, decomposition products, or both. No N—H modes were distinguishable in any samples.

Decreasing the aluminum content of the precursor gel was found to increase the overall crystallinity of the product and affected the phase of crystalline impurities. For a series of crystals with Si:Al ratios ranging from 42 to 248, the Al:K ratio varied (non-systematically) between 0.9 and 1.7. Careful control of the gel processing conditions improved the reproducibility and elimination of impurities.

Other experiments were performed to determine the effect of total water content on crystallinity (see Table 4). It was found that there was a minimum water to gel ratio needed for crystallization but no maximum was observed. The ratio of the mass of water to the mass of gel needed for reaching the saturation vapor pressure of water in these experiments was 2.3. Similar to the behavior observed by Matsukata et. al., [28] crystallization did not occur until several times this amount (see Table 4). Our data differs, however, in that we did not observe an upper threshold in the water to gel ratio.

Matsukata et. al., [28], in DGC (water vapor only) synthesis, found that there is both an upper and lower threshold in the water to gel ratio beyond which no crystalline product is obtained. The lower threshold was found to be several times the amount of water needed to reach the saturation vapor pressure within the reaction vessel. It was speculated that this enables only localized adsorption or condensation to take place, which facilitates crystallization. The upper threshold was related to the amount of water that would allow a continuous phase of water to condense on the gel. A continuous phase of water enables the structure directing agent (SDA) to desorb from the surface of the gel into the liquid phase and either alter or eliminate the gel-SDA interaction needed for crystallization. Thoma et. al., [22] in a VPT (water and organic vapor) system suggested that the lower water threshold also related to a minimum amount of water needed to enable bond cleavage and molecular migration, i.e. to provide charge balancing while molecular rearrangement occurs. Hence, our findings suggest that the vapor phase organics prevent adsorption of excess water and possibly also provide charge balancing during molecular rearrangement.

Figure 3:
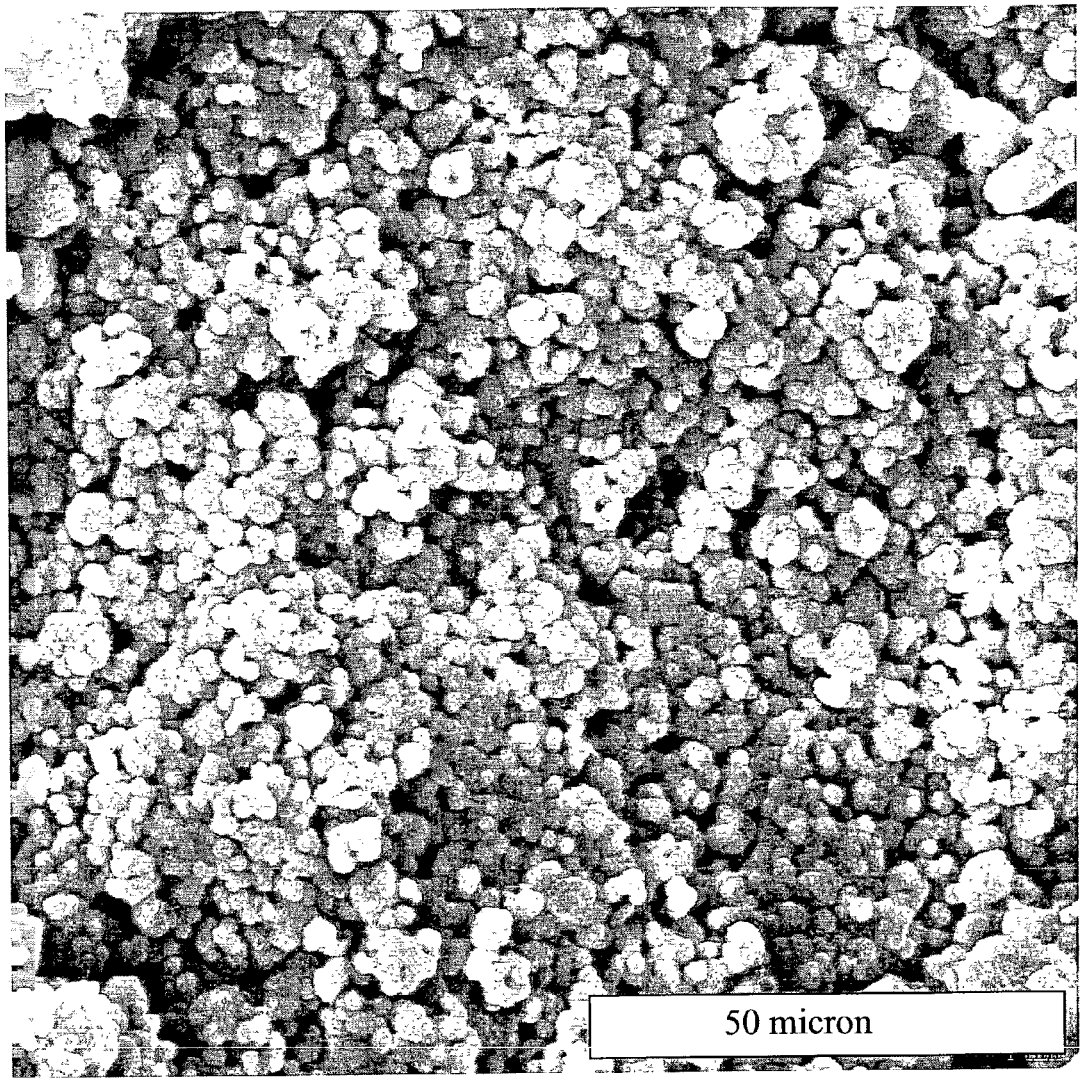
FIG. 3 shows a SEM image of an un-supported ZSM-22 membrane produced by an embodiment of the present invention.
Figure 4:
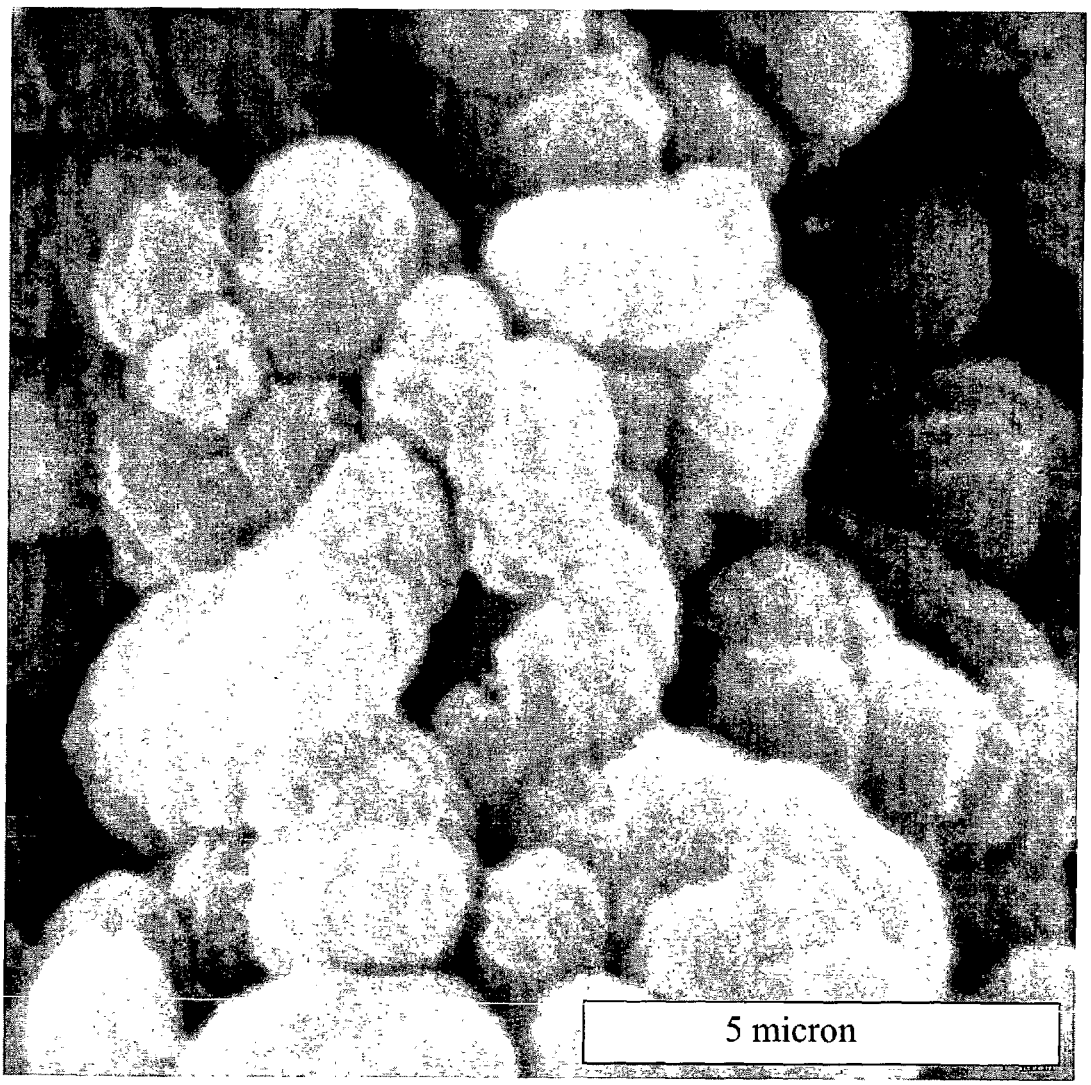
FIG. 4 shows a SEM image of an un-supported ZSM-22 membrane produced by an embodiment of the present invention.

Catalytic membranes were prepared for 1-butene isomerization experiments (experiment 25, aluminum metal derived gel, 170° C., 1 $Et_2N$: $3H_2O$, 7 days). Chemical, X-ray, density, and thermal analyses of the crystals grown in membrane form showed nearly identical properties as for the bulk crystals. The dimensions of the disc did not change as a result of crystallization, although the precursor gel was transformed into intergrown spheroidal clusters of crystals with void space in between. Typical discs were approximately 0.1 inches thick and 0.5 inches in diameter. SEM images of a ZSM-22 membrane are shown in FIGS. 3 and 4. The bulk density and helium density of the crystalline membranes was 0.77 g/cc and 1.93 g/cc, respectively. No mechanical strength testing was performed on the membranes, however they were of sufficient strength to allow handling and use without breakage or degradation.

The results of the 1-butene isomerization experiments are presented in Table 5, along with results from other research for comparison [6,14]. It can be seen that the ZSM-22 membrane has similar catalytic properties to the crystals synthesized in bulk with total conversions in excess of 60% and isobutene selectivities of 27–37%. The highest WHSV yielded the highest selectivity as observed elsewhere [15]. The slight increase in conversion at high WHSV is inconstant with trends observed elsewhere [6] and is attributed to experimental error. The decreased activity of the membrane relative to the reported data is likely due to the lower aluminum content; reduced acidity of ZSM-22 catalysts has previously been shown to lower activity toward 1-butene isomerization [14].

Furthermore, since the bulk and membrane crystal properties are nearly identical, the same procedures currently used to modify bulk ZSM-22 crystals by incorporating or substituting certain elements in order to adapt them for specific processes, such as enhancing activity towards specific reactions. Ion exchange, pore ion exchange, framework exchange, synthesis modification to incorporate other elements into the framework, and noble metal doping/impregnation (e.g., with platinum), may be used to modify the ZSM-22 crystals (in both bulk and membrane form). Elements suitable for modifying ZSM-22 include K, H, Mg, Zn, V, Ga, and Pt. For example, Mg may be substituted for Al during post-synthesis framework modification. Alternatively, H, Zn, Ga may be substituted for the as-synthesized K during pore element ion-exchange. Alternatively, V and/or Ga may be substituted in to the framework during synthesis.

Many zeolite crystals are ion exchangeable once crystallized. For example, the crystalline powder may be mixed with a 10% aqueous solution of a salt (e.g., NaNO3), and stirred while heated at 90° C. for 1 hour, then filtered and washed with deionized water and air dried. This process may be repeated two times.

In summary, ZSM-22 can be synthesized via vapor phase transport crystallization as fully crystalline bulk crystals and as an unsupported membrane. The use of aluminum metal as the aluminum source for preparation of the precursor gel or treatment of aluminum tri-sec butoxide derived precursor gels with 1–6 diaminohexane reduced the formation of crystalline impurities, increased the overall crystallinity, and increased reproducibility. ZSM-22 crystals were prepared with a wide range of silicon to aluminum ratios, which did not affect the final diethyl amine content. Careful control over synthesis conditions and methodology during synthesis was improved reproducibility. The ZSM-22 catalytic membrane compares favorably by 1-butene isomerization to the bulk ZSM-22 crystals prepared by traditional methods.

TABLE 1

Synthesis conditions versus product for ASB derived gels with Si:Al = 182

| Exp't | Temperature (° C.) | Time (days) | Solvent mixture | Product (listed in order of decreasing quantity) |
|---|---|---|---|---|
| 1 | 160 | 5 | 1En:2Et$_3$N:2H$_2$O | amorphous, ZSM-48 |
| 2 | 175 | 5 | 1En:2Et$_3$N:2H$_2$O | amorphous, ZSM-48 |
| 3 | 190 | 5 | 3Aniline:2H$_2$O | quartz, cristobalite, amorphous |
| 4 | 190 | 5 | 1Aniline:2Et$_3$N:2H$_2$O | quartz, cristobalite, ZSM-5 |
| 5 | 160 | 7 | En | amorphous, ZSM-48 |
| 6 | 160 | 7 | 3En:2H$_2$O | amorphous, ZSM-48 |
| 7 | 175 | 7 | 1DAP:2Et$_3$N:2H$_2$O | ZSM-48 |
| 8 | 175 | 7 | 3DAP:2H$_2$O | ZSM-48 |
| 9 | 160 | 7 | Et$_2$N | amorphous |
| 10 | 160 | 7 | 3Et$_2$N:2H$_2$O | ZSM-22, ZSM-48, amorphous |
| 11 | 130 | 11 | 3Et$_2$N:1H$_2$O | ZSM-22, amorphous |
| 12 | 130 | 11 | H$_2$O | amorphous |
| 13 | 130 | 11 | 1Et$_2$N:3H$_2$O | amorphous |
| 14 | 170 | 11 | 3Et$_2$N:1H$_2$O | cristobalite |
| 15 | 170 | 11 | 1Et$_2$N:3H$_2$O | ZSM-22 |

TABLE 1-continued

Synthesis conditions versus product for ASB derived gels with Si:Al = 182

| Exp't | Temperature (° C.) | Time (days) | Solvent mixture | Product (listed in order of decreasing quantity) |
|---|---|---|---|---|
| 16 | 170 | 11 | $H_2O$ | cristobalite, quartz |
| 17 | 180 | 11 | $1Et_2N:3H_2O$ | cristobalite |
| 18 | 170 | 4 | $1Et_2N:3H_2O$ | amorphous |
| 19 | 170 | 8 | $1Et_2N:3H_2O$ | quartz, ZSM-22, ZSM-5 |
| 20 | 170 | 12 | $1Et_2N:3H_2O$ | ZSM-22, cristobalite |
| 21 | 160 | 12 | $1Et_2N:3H_2O$ | ZSM-22, quartz, cristobalite |
| 22 | 150 | 12 | $1Et_2N:3H_2O$ | amorphous |

TABLE 2

Synthesis conditions versus product for aluminum metal derived gels with Si:Al = 115

| Exp't | Temperature (° C.) | Time (days) | Solvent mixture | Product (listed in order of decreasing quantity) |
|---|---|---|---|---|
| 23 | 170 | 7 | $H_2O$ | amorphous |
| 24 | 170 | 7 | $3Et_2N:1H_2O$ | ZSM-22, Beta |
| 25 | 170 | 7 | $1Et_2N:3H_2O$ | ZSM-22 |
| 26 | 170 | 12 | $1Et_2N:3H_2O$ | ZSM-22 |

TABLE 3

Synthesis conditions versus product for ASB derived gels pretreated in 1M DAH

| Exp't | Temperature (° C.) | Time (days) | Precursor Al:Si ratio | Solvent mixture | Product (listed in order of decreasing quantity) |
|---|---|---|---|---|---|
| 30 | 170 | 12 | 1:85 | $1Et_2N:3H_2O$ | ZSM-22 |
| 31 | 170 | 12 | 1:85 | $H_2O$ | ZSM-22, amorphous |
| 32 | 170 | 12 | 1:61 | $1Et_2N:3H_2O$ | ZSM-22 |
| 33 | 170 | 12 | 1:61 | $H_2O$ | amorphous, ZSM-22 |
| 34 | 170 | 12 | 1:44 | $1Et_2N:3H_2O$ | ZSM-22, amorphous |
| 35 | 170 | 12 | 1:44 | $H_2O$ | amorphous, ZSM-22 |

TABLE 4

Mass of water to mass of precursor gel for ASB derived gels, Si:Al = 99, 170 ° C., 12 days, $1Et_2N:3H_2O$.

| Mass of water / mass of gel | Product |
|---|---|
| 1.4 | amorphous |
| 6.6 | amorphous |
| 13.5 | ZSM-22 (fully crystalline) |
| 20.0 | ZSM-22 (fully crystalline) |
| 26.7 | ZSM-22 (fully crystalline) |
| 33.3 | ZSM-22 (fully crystalline) |

TABLE 5

1-butene isomerization results

| Sample | total conversion (%) | isobutene selectivity (%) | time on stream (minutes) | WHSV ($h^{-1}$) | temperature (° C.) | Si:Al |
|---|---|---|---|---|---|---|
| This study | 61 | 27 | 55 | 2.8 | 420 | 115 |
| This study | 62 | 27 | 235 | 2.8 | 420 | 115 |
| This study | 64 | 37 | 235 | 17.3 | 420 | 115 |
| Byggningsback Suib [6] | 46 | 38 | 30 | 150.0 | 400 | 53 |
| Suib [6] | 70 | 34 | 50 | 4.6 | 420 | 45 |
| Suib [6] | 66 | 42 | 230 | 4.6 | 420 | 45 |

REFERENCES

[1] S. A. I. Barri, G. W. Smith, D. White, and D. Young, Nature 312 (1984) 533.
[2] L. M. Parker and D. M. Bibby, Zeolites 3 (1983) 8.
[3] A. Araya and B. M. Lowe, Zeolites 4 (1984) 280.
[4] G. T Kokotailo, J. L. Schlenker, F. G. Dwyer, and E. W. Valyocsik, Zeolites, 5 (1985) 349.
[5] C. A. Fyfe, G. T. Kokotailo, H. Strobl, C. S. Pasztor, G. Barlow, and S. Bradley, Zeolites 9 (1989) 531.
[6] M. W. Simon, S. L. Suib, and C. O'Young, Journal of Catalysis, 147 (1994) 484.

[7] S. Ernst, J. Weitkamp, J. A. Martens, and P. A. Jacobs, Applied Catalysis 48 (1989) 137.

[8] J. F. Denayer, W. Souverijns, P. A. Jacobs, J. A. Martens, and G. V. Baron, J. Phys. Chem. B, 102 (1998) 4588.

[9] G. Sastre, A. Chica, and A. Corma, Journal of Catalysis, 195 (2000) 227.

[10] P. Raybaud, A. Patrigeon, and H. Toulhoat, Journal of Catalysis 197 (2001) 98.

[11] K. C. Park, S. K. Ihm, Applied Catalysis A: General 203 (2000) 201.

[12] N. Kumar, L. E. Lindfors, and R. Byggningsbacka, Applied Catalysis A: General 139 (1996) 189.

[13] M. Chatterjee, D. Bhattacharya, N. Venkatathri, and S. Sivasanker, Catalysis Letters 35 (1995) 313.

[14] S. H. Baeck, K. M. Lee, W. Y. Lee, Catalysis Letters 52 (1998) 221.

[15] R. Byggningsbacka, L. E. Lindfors, and N. Kumar, Ind. Eng. Chem. Res. 36 (1997) 2990.

[16] M-H. Kim, H—X. Li, and M. E. Davis, Microporous Materials, 1 (1993) 191.

[17] N. Nishiyama, K. Ueyama, and M. Matsukata, Microporous Materials 7 (1996) 299.

[18] R. Bandyopadhyay, Y. Kubota, N. Sugimoto, Y. Fukushima, and Y. Sugi, Microporous and Mesoporous Materials, 32 (1999) 81.

[19] P. R. H. P. Rao, K. Ueyama, M. Matsukata, Applied Catalysis A—General, 166 (1998) 97.

[20] A. Bhaumik and T. Tatsumi, Microporous and Mesoporous, 34 (2000) 1.

[21] R. Bandyopadhyay, Y. Kubota, M. Ogowa, N. Sugimoto, Y. Fukushima, and Y. Sugi, Chemistry Letters 4 (2000) 300.

[22] S. G. Thoma and T. M. Nenoff, Microporous and Mesoporous Materials 41 (2000) 295.

[23] S. D. Hellring and D. L. Stern, U.S. Pat. No. 6,207,871 (2001).

[25] J. A. Rodriguez-Carvajal, in Collected Abstracts of Powder Diffraction Meeting; Toulouse, France; 1990, 127.

[26] B. Marler, Zeolites 7 (1987) 393.

[27] M. May, M Asomoza, T. Lopez, and R. Gomez, Chem Mater. 9 (1997) 2395.

[28] M. Matsukata, M. Ogura, T. Osaki, P. Raja, P. Rao, M. Nomura, and E.=Kikuchi, Topics in Catalysis 9 (1999) 77–92.

The particular examples discussed above are cited to illustrate particular embodiments of the invention. Other applications and embodiments of the apparatus and method of the present invention will become evident to those skilled in the art. For example, the synthesis processes described above may be used to grow thin films or membranes of ZSM-22 crystals on a pre-existing substrate, such as a porous ceramic (e.g., alumina), porous metallic substrate, etc.

The actual scope of the invention is defined by the claims appended hereto.

What is claimed is:

1. A process for synthesizing ZSM-22 zeolite crystals comprising, in the order presented:
    a) preparing a precursor gel containing all of the elemental constituents of ZSM-22 by mixing a solution containing a source of aluminum, an alcohol, a source of silica, a base and water, whereby a precursor gel forms;
    b) drying the precursor gel;
    c) converting the dried precursor gel into a powder; and
    d) exposing the powdered dried precursor gel to vapors of a solvent mixture at a temperature and exposure time sufficient to form ZSM-22 zeolite crystals.

2. The process of claims 1, wherein the source of aluminum comprises aluminum tri-sec butoxide (ASB).

3. The process of claim 1, wherein the source of silica comprises tetramethylorthosilicate (TMOS).

4. The process of claim 1, wherein the alcohol comprises an alcohol selected from 2-propanol, butanol, and iso-butanol, and combinations thereof.

5. The process of claim 1, wherein the base comprises KOH or NaOH.

6. The process of claim 1, wherein step d) comprises exposing the powdered precursor gel to vapors of a solvent mixture in an autoclave heated at a temperature above the boiling points of the solvents in the solvent mixture, and for an exposure time sufficient to form ZSM-22 zeolite crystals.

7. The process of claim 6, wherein the autoclave is heated from approximately 130 to approximately 190 C during step d).

8. The process of claim 1, further comprising prior to step d) consolidating the powdered precursor gel into a semi-cohesive body, without using any binder phase.

9. The process of claim 8, further comprising applying pressure to the powdered precursor gel of a sufficient magnitude to form the semi-cohesive body.

10. The process of claim 9, further comprising placing the powdered precursor gel into a rigid die and applying a uniaxial pressure of between about 5000 psi and about 10,000 psi.

11. The process of claim 1, further comprising preparing a slurry containing the dried powdered precursor gel and then slip-casting the slurry in a mold to form a semi-cohesive body without using any binder phase, prior to performing step d).

12. The process of claim 11, wherein the slurry comprises a dispersing agent selected from water, a polar solvent, an alcohol, and tetrahydrofuran (THF), and combinations thereof.

13. The process of claim 1, wherein the precursor gel comprises a composition with a molar ratio of approximately 1 Al:10–15 K: 40–250 Si.

14. The process of claim 1, wherein the precursor gel comprises a composition with a molar ratio of approximately 1 Al:12 K 182 Si.

15. The process of claim 1, wherein the solvent mixture comprises a mixture of water and an organic solvent selected from ethylenediamine (En), triethylamine ($Et_3N$), diethylamine ($Et_2N$), aniline, and diaminopropane (DAP), and combinations thereof.

16. The process of claim 1, wherein the solvent mixture comprises diethylamine and water in a molar ratio of 1 diethylamine:$3H_2O$.

17. The process of claim 16, wherein the autoclave temperature is approximately 170 C and the exposure time is approximately 11 days.

18. The process of claim 16, wherein the ZSM-22 zeolite crystals comprise a composition with a molar ratio of approximately:

115 $SiO_2$:0.5$Al_2O_3$:0.8$M_2O$:5.6$Et_2N$:18.0$H_2O$ if M=monovalent cation; or 115 $SiO_2$:0.5$Al_2O_3$:0.8MO:5.6$Et_2N$, 18.0; $H_2O$ if M=divalent cation.

19. The process of claim 1, wherein the ZSM-22 zeolite crystals have been modified with an element selected from K, H, Mg, Zn, V, Ga, and Pt, and combinations thereof.

20. The process of claim 19, wherein the ZSM-22 zeolite crystals have been ion exchanged under aqueous condition with alkali or alkali earth cations.

21. The process of claim 19, wherein Mg is substituted for Al during post-synthesis framework modification of the ZSM-22 zeolite crystals.

22. The process of claim 19, wherein at least one of H, Zn, and Ga is substituted for the as-synthesized K during pore element ion-exchange of ZSM-22 zeolite crystals.

23. The process of claim 19, wherein at least one of V and Ga is substituted into the ZSM-22 framework during synthesis of ZSM-22 zeolite crystals.

24. The process of claim 1, wherein the precursor gel has a molar ratio of approximately 1 Al:12.5 K:182 Si.

25. The process of claim 1, wherein the dried precursor gel contains less than wt % of water.

26. The process of claim 1, further comprising rinsing the ZSM-22 zeolite crystals formed after autoclaving in step d) in water, methanol, and acetone, and air drying.

27. The process of claim 1, further comprising calcining the ZSM-22 crystals formed in step d).

28. The process of claim 27, wherein calcining the ZSM-22 crystals comprises heating the ZSM-22 crystals at approximately 550 C for about 1 hour in an oxygen atmosphere.

29. The process of claim 28, wherein the ratio of the mass of water to the mass of the precursor gel is greater than approximately 13.5.

30. The process of claim 1, wherein the precursor gel formed in step a) is treated with 1,6-diaminohexane (DAH).

31. A process for synthesizing ZSM-22 zeolite crystals comprising, in the order presented:
   a) preparing an precursor gel containing all of the elemental constituents of ZSM-22 by:
      (1) preparing a solution of base and water;
      (2) dissolving an equivalent molar amount of aluminum metal into the aqueous base solution; and
      (3) adding the product produced by step (2) to a mixture of a source of silica and an alcohol; whereby the precursor gel forms;
   b) drying the precursor gel;
   c) converting the dried precursor gel into a powder; and
   d) exposing the powdered dried precursor gel to vapors of a solvent mixture at a temperature and exposure time sufficient to form ZSM-22 zeolite crystals.

32. The process of claim 31, wherein the source of silica comprises tetramethylorthosilicate (TMOS).

33. The process of claim 31, wherein the alcohol comprises an alcohol selected from 2-propanol, butanol, and iso-butanol, and combinations thereof.

34. The process of claim 31, wherein the base comprises KOH or NaOH.

35. The process of claim 31, wherein the precursor gel formed in step a) is treated with 1,6-diaminohexane (DAH).

36. The process of claim 35, wherein the precursor gel comprises a Al:Si molar ratio of 1:44 to 1:85.

37. The process of claim 31, wherein the solvent mixture comprises a mixture of diethylamine and water in a molar ratio of 1 diethylamine: 3 $H_2O$.

38. The process of claim 37, wherein the autoclave temperature is approximately 170 C and the exposure time is approximately 11 days.

39. The process of claim 31, wherein the precursor gel comprises a Al:Si molar ratio of approximately 115.

40. The process of claim 31, wherein the Si:Al molar ratio of the precursor gel is between approximately 42 and approximately 248.

41. The process of claim 31, further comprising prior to step d) consolidating the powdered precursor gel into a semi-cohesive body, without using any binder phase.

42. A ZSM-22 crystalline membrane produced by the process of claim 8.

43. A ZSM-22 crystalline membrane produced by the process of claim 41.

44. The product of claim 42, wherein the ZSM-22 crystalline membrane has a thickness greater than approximately 0.1 inches.

45. The product of claim 42, wherein the ZSM-22 crystalline membrane has a bulk density of approximately 0.77 g/cc and a helium density of approximately 1.9 g/cc.

46. The product of claim 42, wherein the ZSM-22 crystalline membrane has a bulk density of between ⅓ and ⅔ the density of a ZSM-22 crystal.

47. An industrial process for treating a substance comprising passing the substance through a ZSM-22 crystalline membrane produced by the process of claim 8.

48. An industrial process for treating a substance comprising passing the substance through a ZSM-22 crystalline membrane produced by the process of claim 41.

49. An apparatus for treating a substance, comprising means for holding a ZSM-22 crystalline membrane; and means for passing the substance through the membrane.

50. An apparatus for treating a substance, comprising means for holding an un-supported ZSM-22 crystalline membrane; and means for passing the substance through the un-supported membrane.

51. The process of claim 1, further comprising synthesizing the ZSM-22 crystals on a substrate.

52. The process of claim 31, further comprising synthesizing the ZSM-22 crystals on a substrate.

* * * * *